United States Patent
Hong et al.

(10) Patent No.: US 6,602,650 B2
(45) Date of Patent: Aug. 5, 2003

(54) ORGANIC ANTI-REFLECTIVE COATING POLYMER, ANTI-REFLECTIVE COATING COMPOSITION COMPRISING THE SAME AND METHODS OF PREPARATION THEREOF

(75) Inventors: Sung-eun Hong, Scongnam-shi (KR); Min-ho Jung, Icheon-shi (KR); Jae-chang Jung, Icheon-shi (KR); Geun-su Lee, Icheon-shi (KR); Ki-ho Baik, Icheon-shi (KR)

(73) Assignee: Hynix Semiconductor Inc, Gyunggi-do (KR)

( * ) Notice: Subject to any disclaimer, the term of this patent is extended or adjusted under 35 U.S.C. 154(b) by 0 days.

(21) Appl. No.: 10/099,295

(22) Filed: Mar. 13, 2002

(65) Prior Publication Data

US 2003/0003397 A1 Jan. 2, 2003

Related U.S. Application Data

(63) Continuation of application No. 09/884,250, filed on Jun. 19, 2001.

(30) Foreign Application Priority Data

Jun. 30, 2000 (KR) .......................... 2000-37270

(51) Int. Cl.[7] .................................... G03C 1/76
(52) U.S. Cl. ................. 430/271.1; 430/910; 526/219.6; 526/227; 526/320; 526/326
(58) Field of Search .............. 430/271.1, 905, 430/910; 526/320, 326, 219.6, 227

(56) References Cited

U.S. PATENT DOCUMENTS

| | | | |
|---|---|---|---|
| 4,424,270 A | 1/1984 | Erdmann et al. | |
| 4,822,718 A | 4/1989 | Latham et al. | |
| 5,525,457 A | 6/1996 | Nemoto et al. | |
| 5,674,648 A | 10/1997 | Brewer et al. | |
| 2002/0127789 A1 * | 9/2002 | Hong et al. | |

FOREIGN PATENT DOCUMENTS

| | | |
|---|---|---|
| EP | 1 035 147 A1 | 9/2000 |
| WO | WO 00/01752 | 1/2000 |

* cited by examiner

*Primary Examiner*—Rosemary Ashton
(74) *Attorney, Agent, or Firm*—Marshall, Gerstein & Borun

(57) ABSTRACT

A compound of Formula 10, an organic anti-reflective polymer having the structure of Formula 1 synthesized from the compound of Formula 1 and a preparation method thereof. An anti-reflective coating composition including the above organic anti-reflective polymer, as well as a preparation method of an anti-reflective coating. The anti-reflective coating comprising the disclosed polymer eliminates standing waves caused by the optical properties of lower layers on the wafer and by the changes in the thickness of the photoresist, prevents back reflection and also solves the problem of CD alteration cause by the diffracted and reflected light from such lower layers. Such advantages enable the formation of stable ultrafine patterns suitable for 64M, 256M, 1G, 4G, and 16G DRAM semiconductor devices and an increase of the production yields. Further, it is also possible to control the k value

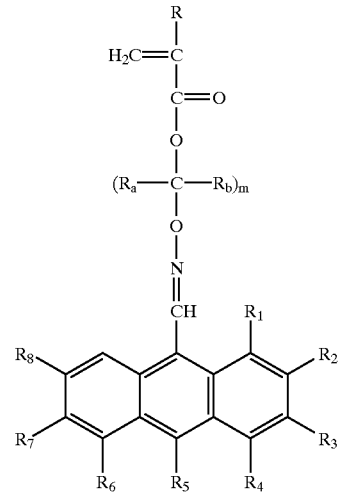

Formula 10

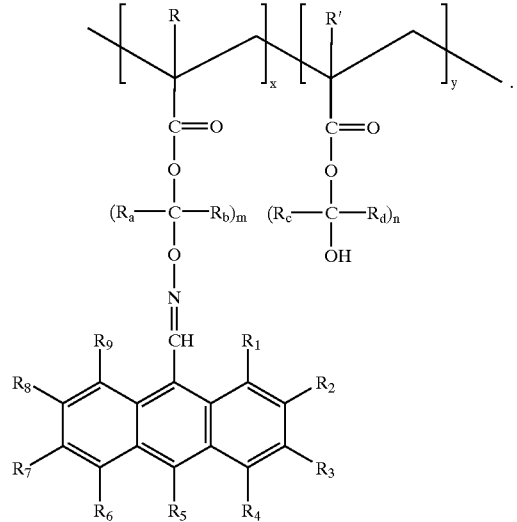

Formula 1

25 Claims, No Drawings

ORGANIC ANTI-REFLECTIVE COATING POLYMER, ANTI-REFLECTIVE COATING COMPOSITION COMPRISING THE SAME AND METHODS OF PREPARATION THEREOF

This is a continuation application of U.S. application Ser. No. 09/884,250, filed Jun. 19, 2001.

BACKGROUND

1. Technical Field

An organic anti-reflective polymer which prevents back reflection of lower film layers and eliminates standing wave that is caused by a thickness change of photoresist and light, in a process for fabricating ultrafine patterns that use photoresist for lithography by using 248 nm KrF and 193 nm ArF. More particularly, the organic anti-reflective polymer is useful for fabricating ultrafine patterns of 64M, 256M, 1G, and 4G DRAM semiconductor devices. A composition containing such organic anti-reflective polymer, an anti-reflective coating layer made therefrom and a preparation method thereof are also disclosed.

2. Description of the Background Art

In a fabrication process of ultrafine patterns for preparing semiconductor devices, standing waves and reflective notching inevitably occur due to the optical properties of lower film layer on the wafer and due to the thickness changes in the photosensitive film. In addition, there is another problem in that a CD (critical dimension) alteration is caused by diffracted and reflected light from the lower film layers. Thus, it has been suggested to introduce anti-reflective coating that prevents back reflection at a lower film layer by introducing organic material with high absorbance at a wavelength range of the light employed as a light source.

Anti-reflective coatings are classified into inorganic and organic anti-reflective coatings depending upon the material used, or into absorptive and interfering anti-reflective coatings based on the operation mechanism. For microlithography using I-line (365 nm wavelength) radiation, inorganic anti-reflective coating are predominantly used, while TiN and amorphous carbon are employed as an absorptive system and SiON are employed as an interfering system.

In a fabrication process of ultrafine patterns using KrF laser, SiON has been mainly used as an inorganic anti-reflective film. However, in the case of an inorganic anti-reflective film, no material has been known which enables the control of the interference at 193 nm, the wavelength of the light source. Thus, there has been great deal of efforts to employ an organic compound as an anti-reflective coating.

To be a good organic anti-reflective coating, the following conditions must be satisfied. First, peeling of the photoresist layer due to the dissolution in a solvent must not take place when conducting a lithographic process. In order to achieve this goal, a molded coating must be designed to form a cross-linked structure without producing any chemical by-product. Second, chemicals such as acid or amine must not come-in or go-out from the anti-reflective coating. This is because when acid migrates from anti-reflective coating, undercutting occurs at a lower part of the pattern while footing may occur when a base such as amine migrates. Third, the etching speed of the anti-reflective coating should be faster than the etching speed of the upper photosensitive film so as to facilitate etching process by using photosensitive film as a mask. Finally, the anti-reflective coating must be as thin as possible to an extent to sufficiently play a role as an anti-reflective coating.

The existing organic anti-reflective materials are mainly divided into two types: (1) polymers containing a chromophore, cross-linking agent (single molecule) that cross-link the polymers and an additive (thermally variable oxidant); and (2) polymers which can cross link themselves and contain a chromophore and an additive (thermally variable oxidant). But these two types of anti-reflective material are problematic in that the control of k value is almost impossible because the content of the chromophore is defined according to the ratio as originally designed at the time of polymerization. Thus, if it is desired to change the k value, the polymer must be resynthesized.

SUMMARY OF THE DISCLOSURE

A novel organic polymer for anti-reflective coating and its preparation method are disclosed.

An anti-reflective coating composition comprising the aforementioned polymer and a preparation method thereof are also disclosed.

A semiconductor device on which a pattern is formed from such an anti-reflective coating by submicrolithography is also disclosed.

DETAILED DESCRIPTION OF THE PRESENTLY PREFERRED EMBODIMENTS

The following compounds having Formulas 1 and 2, respectively are provided which can be used in an anti-reflective coating.

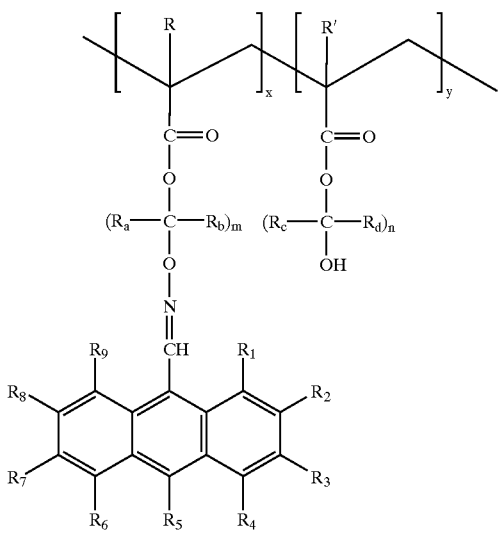

Formula 1

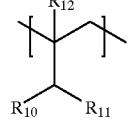

Formula 2 wherein R and R' are each independently hydrogen or methyl;

$R_a$ to $R_d$, $R_1$ to $R_9$ are each independently —H, —OH, —OCOCH$_3$, —COOH, —CH$_2$OH, or substituted or unsubstituted, or straight or branched alkyl or alkoxy alkyl having 1 to 5 carbon atoms;

m and n each represents an integer selected from 1, 2, 3, 4 and 5;

x and y each represents mole fraction from 0.01 to 0.99;

$R_{10}$ and $R_{11}$ are each independently straight or branched substituted $C_{1-10}$ alkoxy;

$R_{12}$ is hydrogen or methyl.

The aforementioned polymer of Formula 1 is prepared from the compound of Formula 10

Formula 10

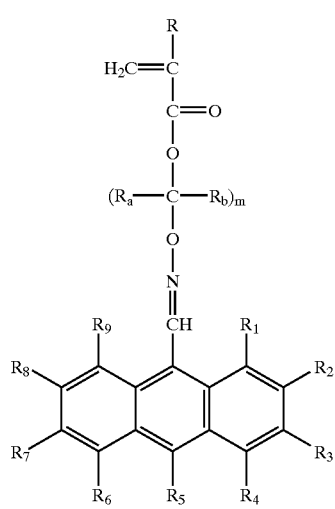

wherein:

R is hydrogen or methyl;

$R_a$, $R_b$, and $R_1$ to $R_9$ are each independently —H, —OH, —OCOCH$_3$, —COOH, —CH$_2$OH, or substituted or unsubstituted, or straight or branched alkyl or alkoxy alkyl having 1 to 5 carbon atoms;

n represents an integer selected from 1, 2, 3, 4 and 5.

The above compound of Formula 10 is prepared by a condensation reaction of anthracene oxime and acrylic monomer in the presence of laurylic acid catalyst as outlined in the following Scheme 1. It is preferred that the above condensation reaction is carried out at a temperature ranging from about 30 to about 80° C. for a time period ranging from about 3 to about 10 hours.

Scheme 1

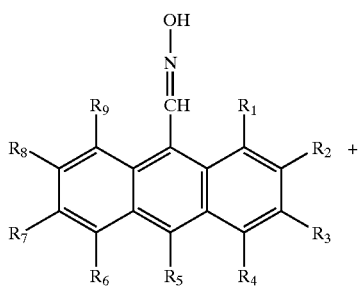

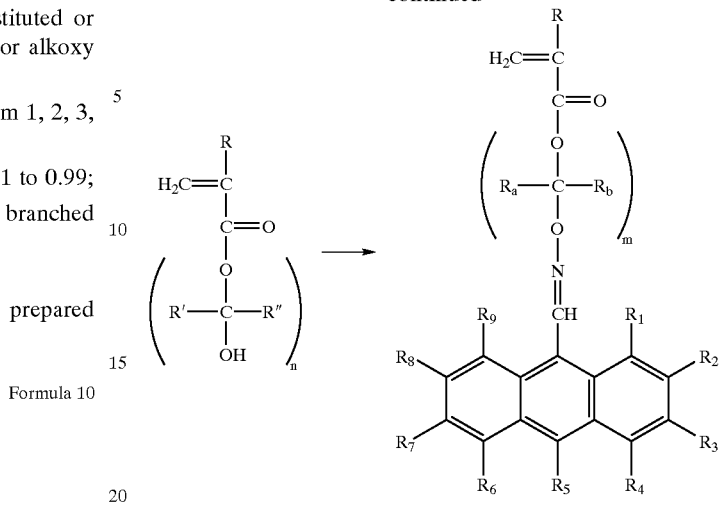

The polymer of Formula 1 is prepared by reacting anthracene methyliminealkylacrylate monomer of Formula 10 with hydroxyacrylate monomer in a solvent and then polymerizing the obtained compound with a polymerization initiator. Suitable solvent is selected from the group consisting of tetrahydrofuran, toluene, methylethylketone, dioxane and mixtures thereof. As a polymerization initiator, it is preferred to use a compound selected from the group consisting of 2,2'-azobisisobutyronitrile, acetylperoxide, laurylperoxide, and t-butylperoxide.

The above polymerization reaction is preferably carried out at a temperature ranging from about 50 to about 90° C. and it is preferred that the mole ratio of each monomer fall within the range of 0.01 to 0.99:0.01 to 0.99.

An anti-reflective coating composition can be characterized as containing the said polymer of Formula 1, or a composition containing both of a polymer of Formula 1 and a compound of Formula 2.

The compound of Formula 2 is prepared by polymerizing (meth)acrolein to obtain poly(meth)acrolein followed by reacting the obtained polymeric product with branched or straight substituted alkyl alcohol having 1 to 10 carbon atoms.

In detail, (meth)acrolein is first dissolved in an organic solvent and added thereto a polymerization initiator to carry out polymerization under vacuum at a temperature ranging from about 60 to about 70° C. for a time period ranging from about 4 to about 6 hours. Then, the obtained polymeric product is reacted with branched or straight substituted alkyl alcohol having 1 to 10 carbon atoms in the presence of trifluoromethylsulfonic acid as a catalyst at a room temperature for a time period ranging from about 20 to about 30 hours.

In the above process, suitable organic solvent is selected from the group consisting of tetrahydrofuran (THF), cyclohexanone, dimethylformamide, dimethylsulfoxide, dioxane, methylethylketone, benzene, toluene, xylene and mixtures thereof. As a polymerization initiator, it can be mentioned 2,2-azobisisobutyronitrile (AIBN), benzoylperoxide, acetylperoxide, laurylperoxide, t-butylperacetate, t-butylhydroperoxide or di-t-butylperoxide. A preferred example of the said alkyl alcohol having 1 to 10 carbon atoms is ethanol or methanol.

A preferred compound of Formula 2 is selected from the group consisting of the compounds of the following Formulas 3 to 6.

Formula 3

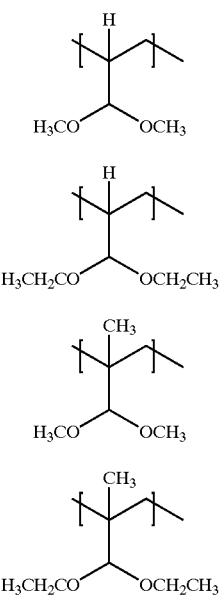

Formula 4

Formula 5

Formula 6

The above compounds of Formulas 3 to 6 are readily cured in the presence of acid and other polymers having alcohol group.

Further, an improved anti-reflective coating composition comprises a polymer of Formula 1, a compound of Formula 2 and an anthracene derivative as an additive. Illustrative, non-limiting examples of the anthracene derivatives (hereinafter, "anthracene derivative additive") is selected from the group consisting of anthracene, 9-anthracenemethanol, 9-anthracenecarbonitrile, 9-antracene carboxylic acid, ditranol, 1,2,10-anthracentriol, anthraflavonic acid, 9-anthraldehydeoxime, 9-anthraldehyde, 2-amino-7-methyl-5-oxo-5H-[1]benzopyrano[2,3-b]pyridine-3-carbonitrile, 1-aminoanthraquinone, anthraquinone-2-carboxylic acid, 1,5-dihydroxyanthraquinone, anthrone, 9-anthryle trifluoromethylketone, 9-alkylanthracene derivatives of the following Formula 7, 9-carboxylanthracene derivatives of the following Formula 8, 1-carboxylanthracene derivatives of the following Formula 9, and mixtures thereof.

Formula 7

Formula 8

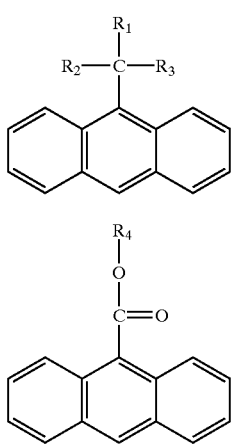

Formula 9

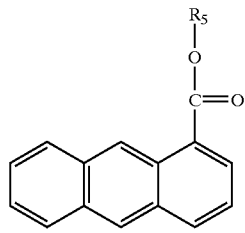

wherein, $R_1$ to $R_5$ are —H, —OH, —CH$_2$OH or substituted or unsubstituted straight or branched alkyl or alkoxyalkyl having 1 to 5 carbon atoms.

A preparation method of an organic anti-reflective coating comprises the steps of dissolving a polymer of Formula 1 and a compound of Formula 2 in an organic solvent, filtering the obtained solution alone or in combination with at least one anthracene derivatives additive as aforementioned, coating the filtrate on a lower layer and hard-baking the coated layer. More particularly, an example of the organic solvent used in this procedure includes ethyl 3-ethoxypropionate, methyl 3-methoxypropionate, cyclohexanone, and propyleneglycolmethylether acetate. It is preferred that the aforementioned solvent is used in an amount ranging from about 200 to about 5,000 wt. % based on the total weight of the anti-reflective coating polymers used. The preferred temperature range for hard-baking is from about 100 to about 300° C.

An improved semiconductor device can be prepared from any of the aforementioned anti-reflective coating compositions.

The polymer of Formula 1 (primary polymer) is synthesized by polymerizing the monomers of Formula 10 which have large sized chromophore so that the obtained polymer of Formula 1 shows a high absorbance at the wavelength of 248 nm. In order to allow improved properties such as good molding property, air-tightness, and dissolution resistance, the compound of Formula 2 (secondary polymer), i.e., a compound capable of forming cross linkage upon the reaction with an alcohol group of the polymer during hard baking step after the coating step, is mixed with the aforementioned primary polymer to form a cross linked product.

In particular, it is possible to freely adjust the k value of the anti-reflective film by controlling the proportion of the primary polymer, because the cross linking agents used in the form of a polymer is designed to maximize the efficiency of the cross linking reaction.

Further, the anti-reflective coating resin has a good solubility in all of the hydrocarbon solvent while it will not dissolve in any of the solvents during a hard-baking step. In addition, no undercutting or footing is experienced in the fabrication process of patterns. Especially, because the anti-reflective coating resin disclosed herein is made from acrylate polymer, which enables higher etching speed relative to, that of the photosensitive film during etching process, the etching selectivity is improved with the anti-reflective coating resin disclosed herein.

The following examples are set forth to illustrate more clearly the disclosed principles and disclosed practices to a person skilled in the art. As such, they are not intended to limit the disclosure, but are illustrative of certain preferred embodiments.

EXAMPLES

Example 1

Preparation of 9-anthracenemethylimineethylacrylate 0.5 mole of 9-anthraldehyde oxyme was dissolved in tetrahydrofuran. The mixture was activated by the addition of a trace amount of dibutyltinlaurate and reacted with 0.5 mole of 2-hydroxyethylacrylate. The reaction solution was filtered, extracted with ethyl acetate, washed with pure water in several times and then dried by using a distillation apparatus under reduced pressure to obtain 9-anthracenemethylimineethylacrylate of the following Formula 11 (yield: 85–90%).

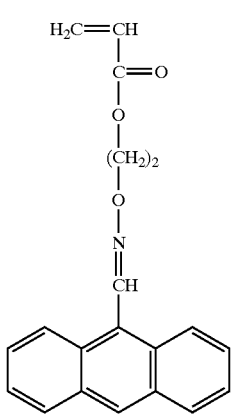

Formula 11

Example 2

Preparation of 9-anthracenemethylimineethylmethacrylate 0.5 mole of 9-anthraldehyde oxyme was dissolved in tetrahydrofuran. The mixture was activated by the addition of a trace amount of dibutyltinlaurate and reacted with 0.5 mole of 2-hydroxyethylmethacrylate. The reaction solution was filtered, extracted with ethyl acetate, washed with pure water in several times and dried by using a distillation apparatus under reduced pressure to obtain 9-anthracenemethylimineethylmethacrylate of the following Formula 12 (yield: 85–90%).

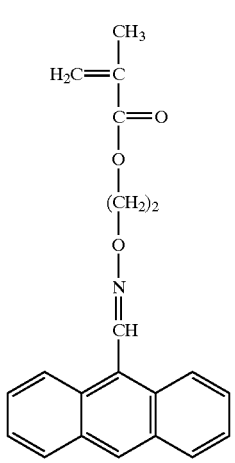

Formula 12

Example 3

Preparation of 9-anthracenemethyliminepropylacrylate 0.5 mole of 9-anthraldehyde oxyme was dissolved in tetrahydrofuran. The mixture was activated by the addition of a trace amount of dibutyltinlaurate and reacted with 0.5 mole of 3-hydroxypropylacrylate. The reaction solution was filtered, extracted with ethyl acetate, washed with pure water in several times and dried by using a distillation apparatus under reduced pressure to obtain 9-anthracenemethyliminepropylacrylate of the following Formula 13 (yield: 85–90%).

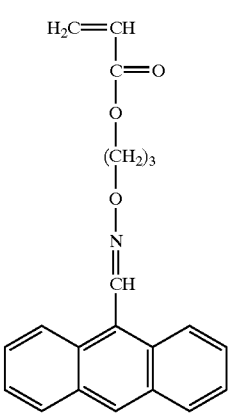

Formula 13

Example 4

Preparation of 9-anthracenemethyliminebutylacrylate 0.5 mole of 9-anthraldehyde oxyme was dissolved in tetrahydrofuran. The mixture was activated by the addition of a trace amount of dibutyltinlaurate and reacted with 0.5 mole of 4-hydroxybutylacrylate. The reaction solution was filtered, extracted with ethyl acetate, washed with pure water in several times and dried by using a distillation apparatus under reduced pressure to obtain 9-anthracenemethyliminebutylacrylate of the following Formula 14 (yield: 85–90%).

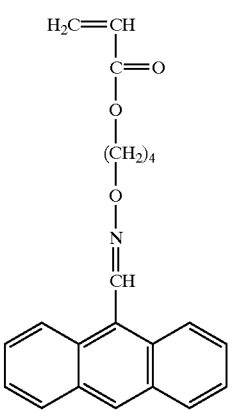

Formula 14

Example 5

Preparation of Poly[9-anthracenemethylimineethylacrylate (2-Hydroxyethylacrylate)]

A 500 ml round bottom flask was charged with 0.5 mole of 9-anthracenemethylimineethylacrylate monomer as prepared in Example 1/0.5 mole of 2-hydroxyethylacrylate while stirring and 300 g of separately prepared tetrahydrofuran was added to a complete mixture. Thereafter, from about 0.1 to about 3.0 g of 2,2'-azobisisobutyronitrile was added and reacted at a temperature ranging from about 60 to about 75° C. under a nitrogen atmosphere for a time period ranging from about 5 to about 20 hours. After the completion of the reaction, the obtained solution was precipitated with ethyl ether or n-hexane solvent and then filtered and dried to obtain poly[9-anthracenemethylimineethylacrylate-(2-hydroxyethyl-acrylate)] resin of the following Formula 15 (yield: 83%).

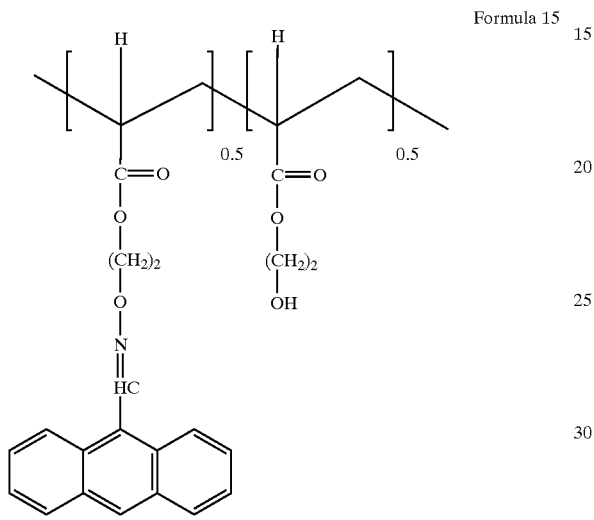

Formula 15

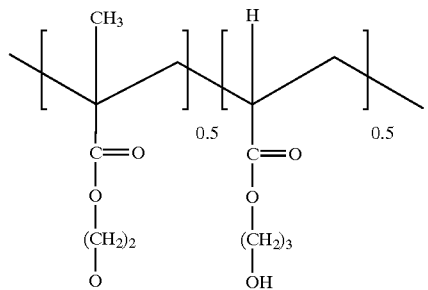

Formula 16

Example 6

Preparation of Poly[9-anthracenemethylimineethylmethacrylate (3-hydroxypropylacrylate)]

To a 500 ml round bottom flask, 0.5 mole of 9-anthracenemethylimineethymethlacrylate monomer as prepared in Example 2/0.5 mole of 3-hydroxypropylacrylate were added while stirring and 300 g of separately prepared tetrahydrofuran was added to a complete mixture. Thereafter, from about 0.1 to about 3.0 g of 2,2'-azobisisobutyronitrile was added and reacted at a temperature ranging from about 60 to about 75° C. under a nitrogen atmosphere for a time period ranging from about 5 to about 20 hours. After the completion of the reaction, the obtained solution was precipitated with ethyl ether or n-hexane solvent and then filtered and dried to obtain poly[9-anthracenemethyl-imineethylmethacrylate-(3-hydroxypropylacrylate)] resin of the following Formula 16 (yield: 82%).

Example 7

Preparation of poly[9-anthracenemethyliminepropyl-acrylate (4-hydroxybutylacrylate)]

To a 500 ml round bottom flask, 0.5 mole of 9-anthracenemethyliminepropylacrylate monomer as prepared in Example 3/0.5 mole of 4-hydroxybutylacrylate were added while stirring and 300 g of separately prepared tetrahydrofuran was added to a complete mixture. Thereafter, from about 0.1 to about 3.0 g of 2,2'-azobisisobutyronitrile was added and reacted at a temperature ranging from about 60 to about 75° C. under a nitrogen atmosphere for a time period ranging from about 5 to about 20 hours. After the completion of the reaction, the obtained solution was precipitated with ethyl ether or n-hexane solvent and then filtered and dried to obtain poly[9-anthracenemethyliminepropylacrylate-(4-hydroxybutylacrylate)] resin of the following Formula 17 (yield: 81%).

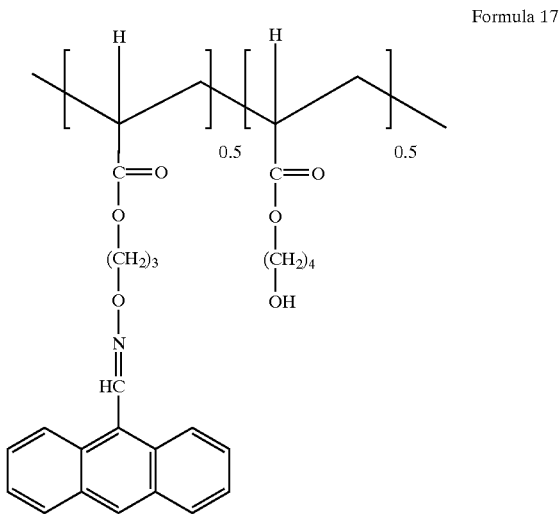

Formula 17

Example 8

Preparation of poly[9-anthracenemethyliminebutylacrylate-(2-hydroxyethylmethacrylate)]

A 500 ml round bottom flask was charged with 0.5 mole of 9-anthracenemethyliminebutylacrylate monomer as prepared in Example 4/0.5 mole of 2-hydroxyethylmethacrylate were added while stirring and 300 g of separately prepared tetrahydrofuran was added to a complete mixture. Thereafter, from about 0.1 to about 3.0 g of 2,2'-azobisisobutyronitrile was added and reacted at a temperature ranging from about 60 to about 75° C. under a nitrogen atmosphere for a time period ranging from about 5 to about 20 hours. After the completion of the reaction, the obtained solution was precipitated with ethyl ether or n-hexane solvent and then filtered and dried to obtain poly[9-anthracenemethyliminebutylacrylate-(2-hydroxyethylmethacrylate)] resin of the following Formula 18 (yield: 79%).

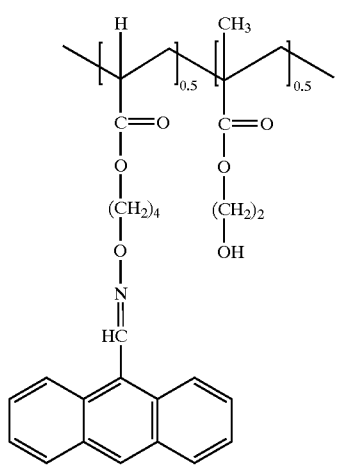

Formula 18

Example 9

Preparation of Anti-Reflective Coating

A polymer of Formula 1 as prepared in one of Examples 1 to 8 and a compound of Formula 2, as exemplified by Formulas 3 to 6 were dissolved in propyleneglycomethylether acetate. The obtained solution, alone or in combination with from about 0.1 to about 30 wt. % of at least one anthracene derivative additive to complete dissolution, was filtered, coated on a wafer, and hard-baked at s temperature range from about 100 to about 300° C. for a time period ranging from about 10 to about 1,000 seconds. Then, a photosensitive film was applied thereon and followed by a routine ultrafine pattern fabrication process.

The cross-linking agent used is preferably in a form of a polymer is designed to maximize the cross-linking efficiency. Further, it is possible to freely modify the k value of an organic anti-reflective coating by controlling the proportion of a primary polymer. Thus, the prior art problem wherein the control of a k value was not possible has been overcome.

Further, the disclosed anti-reflective coating resin dissolves well in all hydrocarbon solvents, while does not dissolve in any of the solvents during a hard-baking step and it does not experience undercutting and footing in a fabrication process of patterns. Particularly, because the disclosed anti-reflective coating resin is composed of acrylate polymer, its etching speed is higher than that of a photosensitive film and thus, the etching selectivity can be improved.

The present invention has been described in an illustrative manner, and it is to be understood the terminology used is intended to be in the nature of description rather than of limitation. It must be understood that many modifications and variations of the present invention are possible in light of the above teachings. Therefore, it is to be understood that within the scope of the appended claims, the invention may be practiced otherwise than as specifically described.

What is claimed is:

1. A compound having the structure of the following Formula 10:

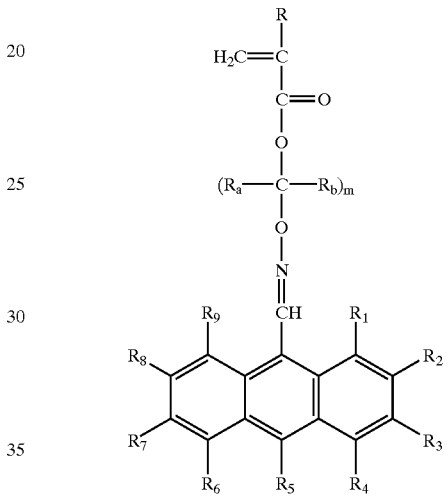

Formula 10 wherein:
R is hydrogen or methyl;
$R_a$ $R_b$, and $R_1$ to $R_9$ are independently selected from the group consisting of —H, —OH, —OCOCH$_3$, —COOH, —CH$_2$OH, alkyl having 1 to 5 carbon atoms and alkoxy alkyl having 1 to 5 carbon atoms: and
m represents an integer selected from the group consisting 1, 2, 3, 4 and 5.

2. The compound of claim 1 which is 9-anthracenemethylimineethylacrylate wherein R, $R_a$ $R_b$, and $R_1$ to $R_9$ are each —H and m is 2.

3. The compound of claim 1 which is 9-anthracenemethylimineethylmethacrylate wherein R is —CH$_3$, $R_a$ $R_b$, and $R_1$ to $R_9$ are each —H and m is 2.

4. The compound of claim 1 which is 9-anthracenemethyliminepropylacrylate wherein R, $R_a$ $R_b$, and $R_1$ to $R_9$ are each —H and m is 3.

5. The compound of claim 1 which is 9-anthracenemethyliminebutylacrylate wherein R, $R_a$ $R_b$, and $R_1$ to $R_9$ are each —H and m is 4.

6. A method for preparing compound of Formula 10 of claim 1, comprising condensing anthracene oxime with acrylic monomer in the presence of a laurylic acid catalyst system.

7. The method of claim 6, wherein the condensing is carried out at the temperature ranging from about 30 to about 80° C.

8. A compound having the structure of the following Formula 1:

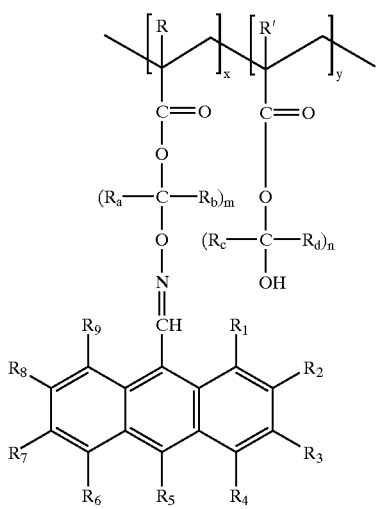

Formula 1 wherein R and R' are each independently hydrogen or methyl;

$R_a$ to $R_d$ and $R_1$ to $R_9$ are each independently selected from the group consisting of —H, —OH, —OCOCH$_3$, —COOH, —CH$_2$OH, alkyl having 1 to 5 carbon atoms and alkoxy alkyl having 1 to 5 carbon atoms;

m and n each represent an integer selected from the group consisting of 1, 2, 3, 4 and 5; and x and y each represent a mole fraction ranging from about 0.01 to about 0.99.

9. The compound of claim 8 which is poly[9-anthracenemethylimineethylacrylate-(2-hydroxyethylacrylate)], wherein R, R', $R_a$ to $R_d$ and $R_1$ to $R_9$ are each hydrogen, m and n are each 2, and x and y are each 0.5.

10. The compound of claim 8 which is poly[9-anthracenemethylimineethylmethacrylate-(3-hydroxypropylacrylate)], wherein R is methyl, R', $R_a$ to $R_d$ and $R_1$ to $R_9$ are each hydrogen, m is 2, n is 3, and x and y are each 0.5.

11. The compound of claim 8 which is poly[9-anthracenemethyliminepropylacrylate-(4-hydroxybutylacrylate)], wherein R, R', $R_a$ to $R_d$ and $R_1$ to $R_9$ are each hydrogen, m is 3, n is 4, and x and y are each 0.5.

12. The compound of claim 8 which is poly[9-anthracenemethyliminebutylacrylate-(2-hydroxyethylmethacrylate)], wherein R' is methyl, R, $R_a$ to $R_d$, and $R_1$ to $R_9$ are each hydrogen, m is 4, n is 2, and x and y are each 0.5.

13. A method for preparing a compound of Formula 1 of claim 8, comprising:

reacting a compound of Formula 10 of claim 1 with hydroxyacrylate monomer in a solvent to obtain a production; and polymerizing the product with a polymerization initiator.

14. The method of claim 13, wherein the solvent is selected from the group consisting of tetrahydrofuran, toluene, methylethylketone, dioxane and mixtures thereof.

15. The method of claim 13, wherein the polymerization initiator is selected from the group consisting of 2,2'-azobisisobutyronitrile, acetylperoxide, lauryl peroxide, t-butylperoxide, and mixtures thereof.

16. The method of claim 13, wherein the polymer is carried out at a temperature ranging from about 50 to about 90° C.

17. An anti-reflective coating composition comprising the compound of Formula 1 of claim 8.

18. An anti-reflective coating composition comprising the compound of formula 1 of claim 8 and a compound of formula 2:

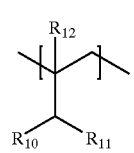

Formula 2 wherein, $R_{10}$ and $R_{11}$ are each independently $C_{1-10}$ alkoxy, and $R_{12}$ is hydrogen or methyl.

19. The composition of claim 18 further comprising an anthracene derivative additive selected from the group consisting of anthracene, 9-anthracenemethanol, 9-anthracenecarbonitrile, 9-antracene carboxylic acid, ditranol, 1,2,10-anthracentriol, anthraflavonic acid, 9-anthraldehydeoxime, 9-anthraldehyde, 2-amino-7-methyl-5-oxo-5H-[1]benzo-pyrano[2,3-b]pyridine-3-carbonitrile, 1-aminoanthraquinone, anthraquinone-2-carboxylic acid, 1,5-dihydroxyanthraquinone, anthrone, 9-anthryle trifluoromethylketone, 9-alkylanthracene derivatives, 9-carboxylanthracene derivatives, 1-carboxylanthracene derivatives and mixtures thereof.

20. A method for preparing an anti-reflective coating comprising:

dissolving the compound of Formula 1 of claim 8 and a compound of Formula 2 in an organic solvent to obtain a solution;

filtering the obtained solution alone or in combination with at least one additive selected from the group consisting of anthracene, 9-anthracenemethanol, 9-anthracenecarbonitrile, 9-antracene carboxylic acid, ditranol, 1,2,10-anthracentriol, anthraflavonic acid, 9-anthraldehydeoxime, 9-anthraldehyde, 2-amino-7-methyl-5-oxo-5H-[1]benzo-pyrano[2,3-b]pyridine-3-carbonitrile, 1-amino-anthraquinone, anthraquinone-2-carboxylic acid, 1,5-dihydroxyanthraquinone, anthrone, 9-anthryle trifluoro-methylketone, 9-alkylanthracene derivatives, 9-carboxylanthracene derivatives, 1-carboxylanthracene derivatives and mixtures thereof to obtain a filtrate;

coating the filtrate on a surface to obtain a coated layer; and hard-baking the coated layer.

21. The method of claim 20, wherein the organic solvent is selected from the group consisting of ethyl-3-ethoxypropionate, methyl 3-methoxypropionate, cyclohexanone, and propyleneglycolmethylether acetate and is used in an amount ranging from about 200 to about 5000 wt. % based on the total weight of the filtrate used.

22. The method of claim 20, wherein the hard-baking step is carried out at a temperature ranging from about 100 to about 300° C.

23. A semiconductor device prepared from the anti-reflective coating composition of claim 17.

24. A semiconductor device prepared from the anti-reflective coating composition of claim 18.

25. A semiconductor device prepared from the anti-reflective coating composition of claim 19.

* * * * *

UNITED STATES PATENT AND TRADEMARK OFFICE
CERTIFICATE OF CORRECTION

PATENT NO.    : 6,602,650 B2
DATED         : August 5, 2003
INVENTOR(S)   : Sung-eun Hong et al.

It is certified that error appears in the above-identified patent and that said Letters Patent is hereby corrected as shown below:

<u>Title page,</u>
Item [57], ABSTRACT, please delete Formula 10 in its entirety and replace with the following Formula 10:

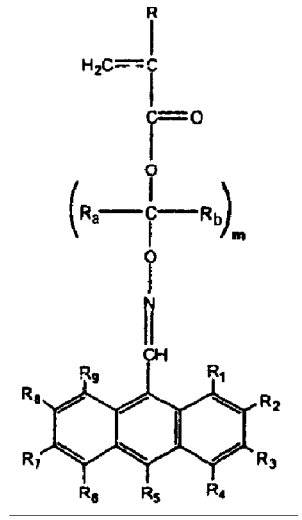

Signed and Sealed this

Twenty-third Day of March, 2004

JON W. DUDAS
*Acting Director of the United States Patent and Trademark Office*